United States Patent
Hwang et al.

(10) Patent No.: US 10,925,686 B2
(45) Date of Patent: Feb. 23, 2021

(54) POSITION INDICATING APPARATUS AND BONE FIXATION APPARATUS INCLUDING THE SAME

(71) Applicant: DAEGU GYEONGBUK INSTITUTE OF SCIENCE AND TECHNOLOGY, Dalseong-gun (KR)

(72) Inventors: Jae Youn Hwang, Dalseong-gun (KR); Jun Young Kim, Suseong-gu (KR); Jihun Kim, Changwon-si (KR); Min Kyu Je, Dalseong-gun (KR); Jae Suk Choi, Namyangju-si (KR)

(73) Assignee: DAEGU GYEONGBUK INSTITUTE OF SCIENCE AND TECHNOLOGY, Dalseong-gun (KR)

( * ) Notice: Subject to any disclaimer, the term of this patent is extended or adjusted under 35 U.S.C. 154(b) by 276 days.

(21) Appl. No.: 15/561,854

(22) PCT Filed: Jun. 8, 2017

(86) PCT No.: PCT/KR2017/005937
§ 371 (c)(1),
(2) Date: Sep. 26, 2017

(87) PCT Pub. No.: WO2017/213425
PCT Pub. Date: Dec. 14, 2017

(65) Prior Publication Data
US 2018/0214240 A1   Aug. 2, 2018

(30) Foreign Application Priority Data
Jun. 8, 2016   (KR) .................. 10-2016-0071281

(51) Int. Cl.
*A61B 90/30* (2016.01)
*A61B 90/35* (2016.01)
(Continued)

(52) U.S. Cl.
CPC .......... *A61B 90/35* (2016.02); *A61B 17/1717* (2013.01); *A61B 17/1725* (2013.01);
(Continued)

(58) Field of Classification Search
CPC .............................. A61B 90/30; A61B 90/35
See application file for complete search history.

(56) References Cited

U.S. PATENT DOCUMENTS

| 8,231,629 | B2 | 7/2012 | Lerner et al. |
| 8,257,409 | B2 | 9/2012 | Schlienger et al. |

(Continued)

FOREIGN PATENT DOCUMENTS

| JP | 9-192138 A | 7/1997 |
| KR | 10-2008-0004490 A | 1/2008 |

(Continued)

OTHER PUBLICATIONS

English translation of the International Search Report dated Sep. 12, 2017 in PCT/KR2017/005937, citing documents AA-AE, AO and AP therein, 2 pages.

*Primary Examiner* — Olivia C Chang
(74) *Attorney, Agent, or Firm* — Oblon, McClelland, Maier & Neustadt, L.L.P.

(57) ABSTRACT

Disclosed is a position indicating apparatus including a main body, a first arm connected to one side of the main body based on a symmetric axis of the main body, a second arm connected to another side of the main body based on the symmetric axis, a first light radiator connected to one end of the first arm to radiate a light, and a second light radiator connected to one end of the second arm to radiate a light, wherein the light radiated from the first light radiator and the light radiated from the second light radiator meet and form an intersection of line.

7 Claims, 10 Drawing Sheets

(51) Int. Cl.
*A61B 90/00* (2016.01)
*G01N 21/17* (2006.01)
*A61B 17/17* (2006.01)
*A61B 90/13* (2016.01)
*A61B 17/72* (2006.01)
*A61B 17/00* (2006.01)
*A61B 34/20* (2016.01)

(52) U.S. Cl.
CPC ............ *A61B 17/725* (2013.01); *A61B 90/00* (2016.02); *A61B 90/13* (2016.02); *G01N 21/17* (2013.01); *A61B 2017/00398* (2013.01); *A61B 2034/2048* (2016.02); *A61B 2090/061* (2016.02)

(56) References Cited

U.S. PATENT DOCUMENTS

| | | |
|---|---|---|
| 2008/0255573 A1 | 10/2008 | Willett |
| 2008/0312702 A1 | 12/2008 | Schlienger et al. |
| 2009/0306665 A1 | 12/2009 | Lerner et al. |
| 2010/0030219 A1 | 2/2010 | Lerner et al. |
| 2010/0323320 A1* | 12/2010 | Takebayashi .......... A61C 1/084 433/75 |

FOREIGN PATENT DOCUMENTS

| | | |
|---|---|---|
| KR | 10-2008-0014960 | 2/2008 |
| KR | 10-2016-0010106 | 3/2016 |

* cited by examiner

POSITION INDICATING APPARATUS AND BONE FIXATION APPARATUS INCLUDING THE SAME

TECHNICAL FIELD

One or more exemplary embodiments relate to a position indicating apparatus and a bone fixation apparatus including the position indicating apparatus.

BACKGROUND ART

A position indicating apparatus may be used in a field requiring a precise work. For example, in a field where a precise insertion technique is required for a small hole, a desired effect may not be achieved even if a slight error occurs. Also, when a tool inserted into the small hole is not able to escape due to precise tolerances, equipment may need to be discarded.

In particular, the position indicating apparatus may be used in a medical field. For example, a nail may be attached to a handle to be used for fixing broken bones in a bone fixation operation. However, once the nail is inserted into the bone, a position of the nail may not be seen by an operator in real time. Thus, the position of the nail in the bone may be recognized using an X-ray or computerized tomography (CT) image. To accurately acquire position information of a bone implant, an image may need to be acquired, which may lead to a radiation exposure of both the operator and the patient. Accordingly, there is a desire for an apparatus to indicate a position without acquiring a real-time X-ray image that causes the radiation exposure during an operation.

For example, Korean Patent Laid-open Publication No. 10-2016-0010106 discloses a position indicator device for surgery.

In general, when drilling on a bone fixed using an intramedullary nail for an operation of a patient, a drill may need to be accurately inserted into a lower end hole or a proximal hole of the nail. Also, an accurate and precise insertion may be required to prevent the drill from penetrating the bone to an outside of an opposite cortex bone. For this, the drilling may be frequently suspended to verify a position of a blade of the drill, which may increase an amount of radiation exposure and an operation time.

Also, Korean Patent Laid-open Publication No. 10-2008-0014960 discloses a surgical depth instrument.

DISCLOSURE OF INVENTION

Technical Goals

An aspect provides a position indicating apparatus for accurately indicating a desired position using a light in various fields such as a construction field, a medical field, and a precise machine field.

Another aspect provides a position indicating apparatus for indicating a position of a target without applying a physical force directly to the target.

Still another aspect provides a bone fixation apparatus for accurately indicating a position of a hole to be drilled on a bone without radiography.

Yet another aspect provides a bone fixation apparatus for indicating a position without restrictions on a space and costs.

Further another aspect provides a bone fixation apparatus and a bone fixation system including the bone fixation apparatus to significantly reduce an error of a direction in which the drill is inserted into a body by measuring a posture of an intramedullary nail and a posture of a drill.

Still another aspect provides a bone fixation apparatus and a bone fixation system including the bone fixation apparatus to provide information on a drill insertion direction to an operator in an intuitively recognizable form.

Technical Solutions

According to an aspect, there is provided a position indicating apparatus including a main body, a first arm connected to one side of the main body based on a symmetric axis of the main body, a second arm connected to another side of the main body based on the symmetric axis, a first light radiator connected to one end of the first arm to radiate a light, and a second light radiator connected to one end of the second arm to radiate a light.

The light radiated from the first light radiator and the light radiated from the second light radiator may meet and form an intersection of line.

The first light radiator and the second light radiator may be configured to rotate in a longitudinal direction and a lateral direction based on a center of the first light radiator and a center of the second light radiator.

The first arm and the second arm may be adjustable in angle based on the symmetric axis of the main body.

The position indicating apparatus may further include a first arm adjusting member interposed between the main body and the first arm to adjust a rotation angle of the first arm, and a second arm adjusting member interposed between the main body and the second arm to adjust a rotation angle of the second arm.

The first light radiator may be adjustable in angle based on a longitudinal axis of the first arm, and the second light radiator may be adjustable in angle based on a longitudinal axis of the second arm.

The main body may include a connecting hole formed internally, and locking guide holes formed on one side surface of the main body and another side surface opposite to the one side surface.

According to another aspect, there is also provided a bone fixation apparatus for indicating a position of an operation, the apparatus including a targeting guide including a through bore on one side, a nail connected to another side of the targeting guide, including a first screw bore aligned with the through bore at a front end, and including a second screw bore at a rear end, and a marker module connected to the targeting guide to indicate a position of the second screw bore.

The marker module may include a main body connected to the targeting guide, and a plurality of light radiators arranged on both sides to be spaced apart based on a symmetric axis of the main body and configured to be adjustable in angle.

Lights radiated from the plurality of light radiators may meet and form an intersection of line so as to indicate the position of the second screw bore, and the intersection of line may be used to indicate an insertion point corresponding to the position of the second screw bore.

The plurality of light radiators may be configured to radiate a linear beam.

The marker module may include a main body connected to the targeting guide, an arm rotatably connected to the main body so as to be adjustable in angle relative to a symmetric axis of the main body, and a laser radiator disposed at one end of the arm to radiate a light toward the second screw bore.

The arm may include a tilting member configured to accommodate the laser radiator and rotate relative to a longitudinal direction of the arm.

The marker module may be configured to acquire nail shape data through three-dimensional (3D) scanning, and the marker module may further includes a radiation adjuster configured to correct motions of the arm and the tilting member based on the nail shape data.

According to still another aspect, there is also provided a bone fixation system for indicating a position of an operation, the system including a targeting guide, a nail having one end connected to the targeting guide and a screw bore at another end, and a drill configured to insert into the screw bore.

The targeting guide or the nail may include an intramedullary nail posture detector configured to measure nail posture information.

The drill may include a drill posture detector configured to measure drill posture information.

An insertion direction of the drill with respect to the screw bore may be corrected based on the measured nail posture information and the measured drill posture information.

The bone fixation system may further include an insertion direction corrector configured to convert the measured posture information into insertion direction information such that an insertion path of the drill is aligned with the screw bore.

The insertion direction corrector may be configured to correct an insertion direction such that a yaw value of nail posture information is perpendicular to a yaw value of drill posture information.

The drill posture detector may be configured to measure an insertion direction in real time, and the insertion direction corrector may be configured to perform conversion into insertion incidence angle information based on the real-time measured insertion direction.

The bone fixation system may further include an indicator to provide the measured nail posture information, the measured drill posture information, the converted insertion direction information, or the converted incident angle information.

According to yet another aspect, there is also provided a bone fixation apparatus for increasing an insertion accuracy, the apparatus including a targeting guide, a nail having one side connected to the targeting guide and a screw bore on another side, and an inertia sensor configured to measure nail posture information including an acceleration of gravity, an angular velocity, or a magnetic field.

The bone fixation apparatus may further include a processor unit configured to the nail posture information measured by the inertia sensor into injection incidence angle information associated with the screw bore such that a drill insertion path is aligned with the screw bore, and a communicator configured to transmit the insertion incidence angle information converted by the processor unit.

The bone fixation apparatus may further include a display configured to receive insertion incidence angle information from the communicator and display a roll, pitch, or yaw value of the received insertion incidence angle information, an insertion inducing indication, or a drill insertion direction.

According to further another aspect, there is also provided a surgical operation method using a bone fixation system, the method including connecting a position indicating apparatus and an intramedullary nail including a targeting guide and a nail connected to one side of the targeting guide and having a screw bore at a lower end, correcting an intersection line that is formed by lights radiated from a plurality of light radiators to be aligned with the screw bore using the position indicating apparatus including the plurality of light, incising a skin and inserting the nail into an incision part of the skin, and inserting a fixing screw into a position indicated by the intersection line formed by the radiated lights.

The surgical operation method may further include correcting a direction in which the fixing screw is inserted into the screw bore based on measured nail posture information and measured drill posture information.

The surgical operation method may further include inserting the fixing screw by positioning a drill such that a drill insertion path is aligned with the screw bore in response to a compensation for the roll value and the yaw value of the measured nail posture information based on the pitch value and the yaw value of the measured drill posture information.

The surgical operation method may further include acquiring intramedullary nail shape data through a 3D scanning and correcting insertion angle and position of the light radiator based on the intramedullary nail shape data before connecting the position indicating apparatus and the intramedullary nail.

Effects

According to an aspect, it is possible to provide a position indicating apparatus for accurately indicating a desired position using a light in various fields such as a construction field, a medical field, and a precise machine field.

According to another aspect, it is possible to provide a position indicating apparatus for indicating a position of a target without applying a physical force directly to the target.

According to still another aspect, it is possible to provide a bone fixation apparatus for accurately indicating a position of a hole to be drilled on a bone without radiography.

According to yet another aspect, it is possible to provide a bone fixation apparatus for indicating a position without restrictions on a space and costs.

According to further another aspect, it is possible to provide a bone fixation apparatus and a bone fixation system including the bone fixation apparatus to significantly reduce a direction in which the drill is inserted into a body by measuring a posture of an intramedullary nail and a posture of a drill.

According to still another aspect, it is possible to provide a bone fixation apparatus and a bone fixation system including the bone fixation apparatus to provide information on a drill insertion direction to an operator in an intuitively recognizable form.

Effects of the position indicating apparatus and a bone fixation apparatus for indicating a position for an operation, and a bone fixation apparatus for increasing an insertion accuracy and a bone fixation system including the bone fixation apparatus are not limited to those mentioned above, and other effects not mentioned are to be obviously understood by those skilled in the art from the following description.

BEST MODE FOR CARRYING OUT THE INVENTION

Figure 1:
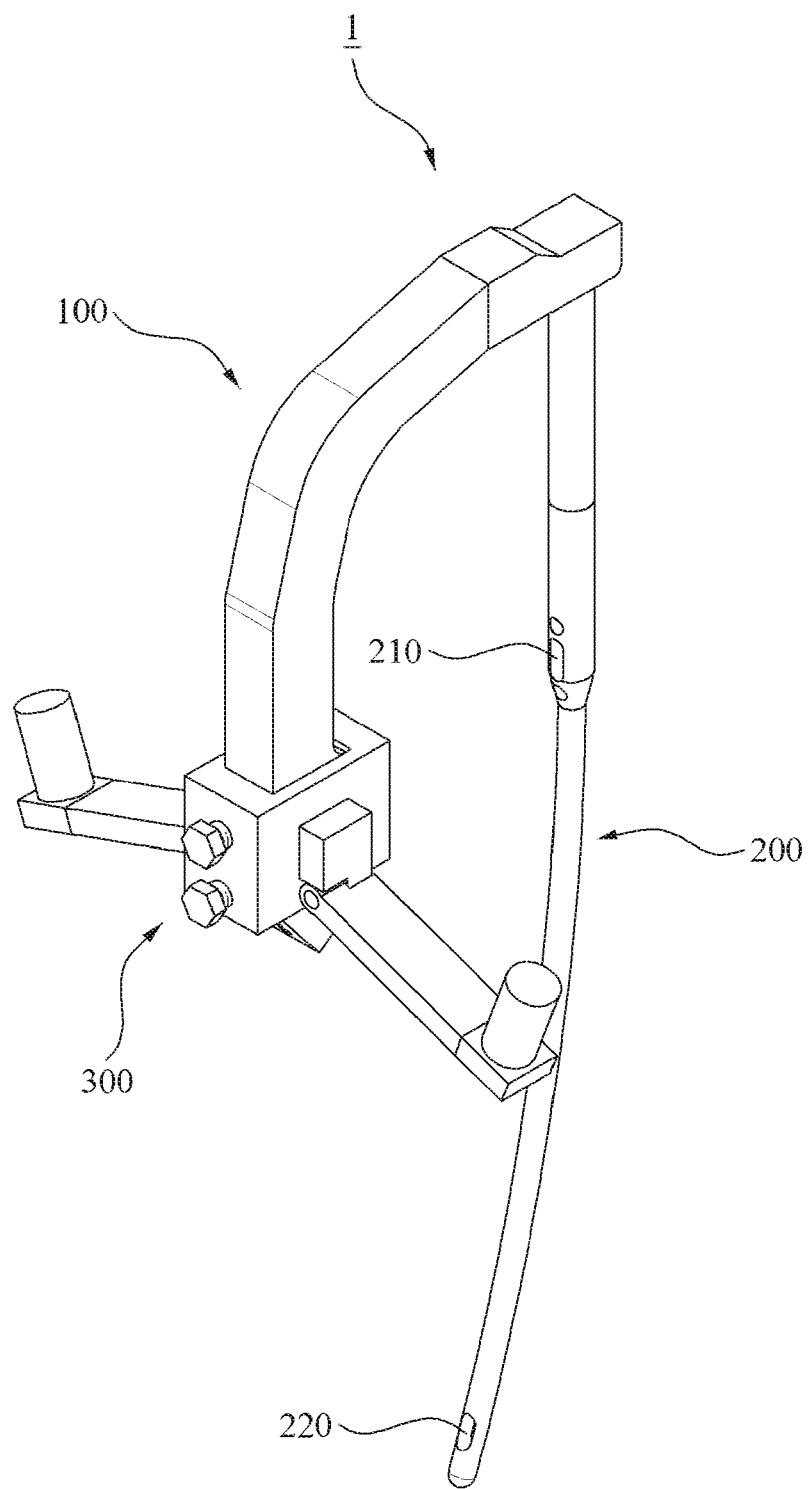
FIG. 1 is a perspective view illustrating a bone fixation apparatus including a position indicating apparatus to indicate a position for an operation according to an example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

When describing the examples with reference to the accompanying drawings, like reference numerals refer to like constituent elements and a repeated description related thereto will be omitted. When it is determined detailed description related to a related known function or configuration they may make the purpose of the examples unnecessarily ambiguous in describing the examples, the detailed description will be omitted here.

Referring to FIGS. 1 through 6, a bone fixation apparatus 1 for indicating a position for an operation may include a targeting guide 100 including a through bore 110 on one side, a nail 200 connected to another side of the targeting guide 100, and a marker module 300 connected to the targeting guide to indicate a position of a second screw bore 220. The nail 200 may include a first screw bore 210 aligned with the through bore 110 at a front end and the second screw bore 220 at a rear end.

A configuration including the targeting guide 100 and the nail 200 connected to the targeting guide 100 may be considered as an intramedullary nail.

Since the nail 200 is inserted into a body, a position of the first screw bore 210 may not be seen from an outside of the body. The through bore 110 may be provided in the targeting guide 100 without restrictions of location. In general, a fixing screw may be inserted into the first screw bore 210 via the through bore 110. Thus, an insertion path may be arranged such that the fixing screw is connected to the first screw bore 210 through the through bore 110 and the first screw bore 210.

The marker module 300 may include a position indicating apparatus configured to radiate a light to the second screw bore as discussed below. Hereinafter, the marker module 300 including the position indicating apparatus will be described. The marker module 300 and the targeting guide 100 may be formed integrally. Also, the marker module 300 may be detachably connected to the targeting guide 100. The marker module 300 may include a connecting hole 350 and locking guide holes 360a, 360b, 360c, and 360d. The connecting hole 350 may be connected to the targeting guide 100 along with the targeting guide 100. A shape of the connecting hole 350 may correspond to a shape of the targeting guide 100. Also, the locking guide holes 360a, 360b, 360c, and 360d may be aligned with the through bore 110 of the targeting guide 100. Through this, the marker module 300 may be connected to the targeting guide 100 through a fixing member (not shown) that penetrates the locking guide holes 360a, 360b, 360c, and 360d, and the through bore 110. In this example, before the marker module 300 is connected to the targeting guide 100, the fixing screw may be connected to the first screw bore 210, and a correction operation of the marker module 300 may be performed before the fixing screw is connected to the first screw bore 210.

The targeting guide 100 may further include a hole (not shown) that is aligned with the locking guide holes 360a, 360b, 360c, and 360d in addition to the through bore 110. The hole may be formed adjacent to the through bore 110 not to interfere with the insertion path of the fixing screw passing through the through bore 110. In this example, the fixing screw may be connected to the first screw bore 210 through the through bore 110 and the first screw bore 210 without need to perform the correction operation of the marker module 300 in advance.

Figure 2:
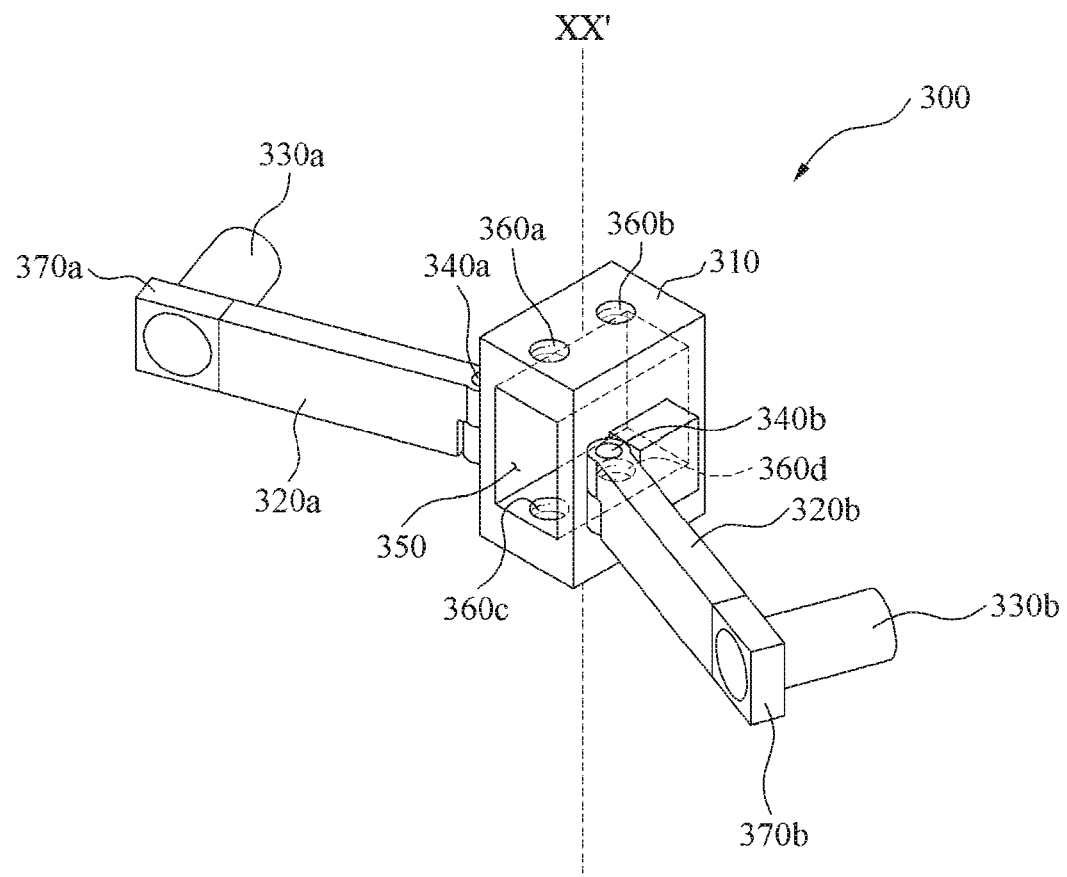
FIG. 2 is a perspective view illustrating a position indicating apparatus according to an example embodiment.
Figure 3:
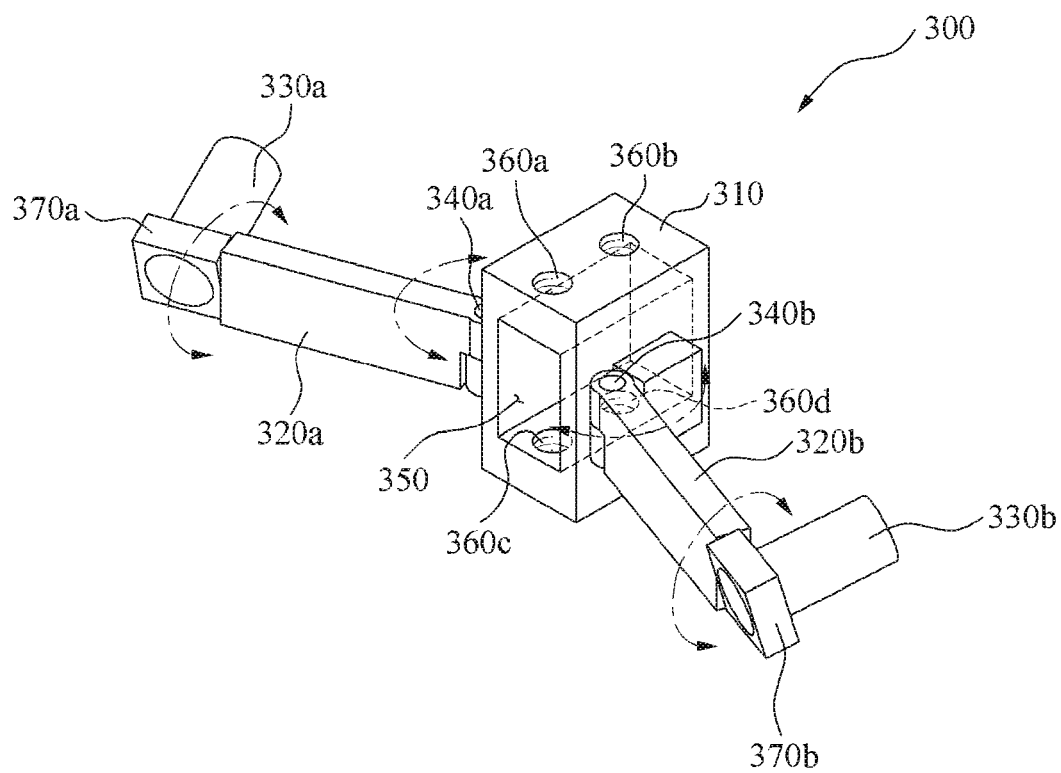
FIG. 3 is a view illustrating an operation of a position indicating apparatus according to an example embodiment.

Referring to FIGS. 2 and 3, the marker module 300 may include a main body 310, a first arm 320a connected to one side of the main body 310 based on a symmetric axis XX' of the main body 310, a second arm 320b connected to another side of the main body 310 based on the symmetric axis XX', a first light radiator 330a connected to one end of the first arm 320a to radiate a light, and a second light radiator 330b connected to one end of the second arm 320b to radiate a light.

The main body 310 may be connected to the targeting guide 100. Specifically, the main body 310 may include the connecting hole 350 therein, and the locking guide holes 360*a*, 360*b*, 360*c*, and 360*d* on one side surface and the other side surface opposite to the one side.

The connecting hole 350 may be provided in various shapes. To be tightly connected to the targeting guide 100, a shape of the connecting hole 350 may correspond to a shape of the targeting guide 100. Also, the connecting hole 350 may be formed to penetrate into the main body 310. In this example, the marker module 300 may also be connected to the targeting guide 100 on another side different from the one side.

The locking guide holes 360*a*, 360*b*, 360*c*, and 360*d* may be formed on one side of the main body 310 and the other side opposite to the one side. A number of the locking guide holes 360*a*, 360*b*, 360*c*, and 360*d* sufficient to be tightly connected to the targeting guide 110 may not be restricted. Also, the locking guide holes 360*a*, 360*b*, 360*c*, and 360*d* may be formed on one side. The locking guide holes 360*a*, 360*b*, 360*c*, and 360*d* may be aligned with the through bore 110 formed on one side of the targeting guide 100. When the targeting guide 100 includes an additional hole (not shown) adjacent to the through bore 110, the locking guide holes 360*a*, 360*b*, 360*c*, and 360*d* may be aligned with the additional hole.

An arm may include the first arm 320*a* and the second arm 320*b*. The first arm 320*a* may be connected to one side of the main body 310 based on the symmetric axis XX'. The second arm 320*b* may be connected to the other side of the main body 310 based on the symmetric axis XX'. The first arm 320*a* and the second arm 320*b* may be spaced apart from each other based on the symmetric axis XX' of the main body 310. A longitudinal direction of the symmetric axis XX' may be, but not limited to, a direction vertical to a plane including the locking guide holes 360*a*, 360*b*, 360*c*, and 360*d*, and also be a direction vertical to a plane including the connecting hole 350.

The first arm 320*a* and the second arm 320*b* may be adjustable in angle based on the symmetric axis XX' of the main body 310 in order to adjust a position to which a light is radiated from a light radiator. Also, the first arm 320*a* and the second arm 320*b* may be rotatably connected to the main body 310 so as to be adjustable in angle. For example, a first arm adjusting member 340*a* may be interposed between the main body 310 and the first arm 320*a*, and a second arm adjusting member 340*b* may be interposed between the main body 310 and the second arm 320*b*.

The first arm adjusting member 340*a* and the second arm adjusting member 340*b* may each be a hinge-type adjusting member. For example, the first arm adjusting member 340*a* and the second arm adjusting member 340*b* may each be a hinged adjusting member disposed on one side of the main body 310. Also, the first arm adjusting member 340*a* and the second arm adjusting member 340*b* may each include an elastic body such as a spring such that the first arm 320*a* and the second arm 320*b* are to be adjustable in angle based on the symmetric axis XX' of the main body 310.

The first arm adjusting member 340*a* and the second arm adjusting member 340*b* may finely adjust the first arm 320*a* and the second arm 320*b*, respectively. The first arm adjusting member 340*a* and the second arm adjusting member 340*b* may be, for example, an adjusting member such as a scaled and graduated clip. Also, the first arm adjusting member 340*a* and the second arm adjusting member 340*b* may be adjusting members controlled by an angle adjustable motor, for example, a servomotor connected to the main body 310. In this example, more precise control of the first arm 320*a* and the second arm 320*b* may be possible. Also, it is possible to indicate a position that minimizes an error in a field requiring a precise operation.

A light radiator may include the first light radiator 330*a* and the second light radiator 330*b* configured to radiate lights. The first light radiator 330*a* and the second light radiator 330*b* may be connected to one end of the first arm 320*a* and one end of the second arm 320*b*, respectively. The first arm 320*a* and the second arm 320*b* may include receivers at one ends such that the first light radiator 330*a* and the second light radiator 330*b* are respectively accepted at the one end of the first arm 320*a* and the one end of the second arm 320*b*. A shape of the receiver may correspond to shapes of the first light radiator 330*a* and the second light radiator 330*b* such that the first light radiator 330*a* and the second light radiator 330*b* are tightly accepted into the receivers at the one end of the first arm 320*a* and the one end of the second arm 320*b*.

Also, the first light radiator 330*a* and the second light radiator 330*b* may be a light radiator that automatically adjusts an angle without adjusting angles of the one end of the first arm 320*a* and the second arm 320*b*. The first light radiator 330*a* and the second light radiator 330*b* may be configured to rotate in a longitudinal direction and a lateral direction relative to a center of the first light radiator and a center of the second light radiator. Also, the first light radiator 330*a* and the second light radiator 330*b* may include motors connected to the main body 310 and allowing angle adjustments of the first light radiator 330*a* and the second light radiator 330*b*. Through this, the first light radiator 330*a* and the second light radiator 330*b* may rotate in the longitudinal direction and the lateral direction relative to the centers thereof.

Figure 4:
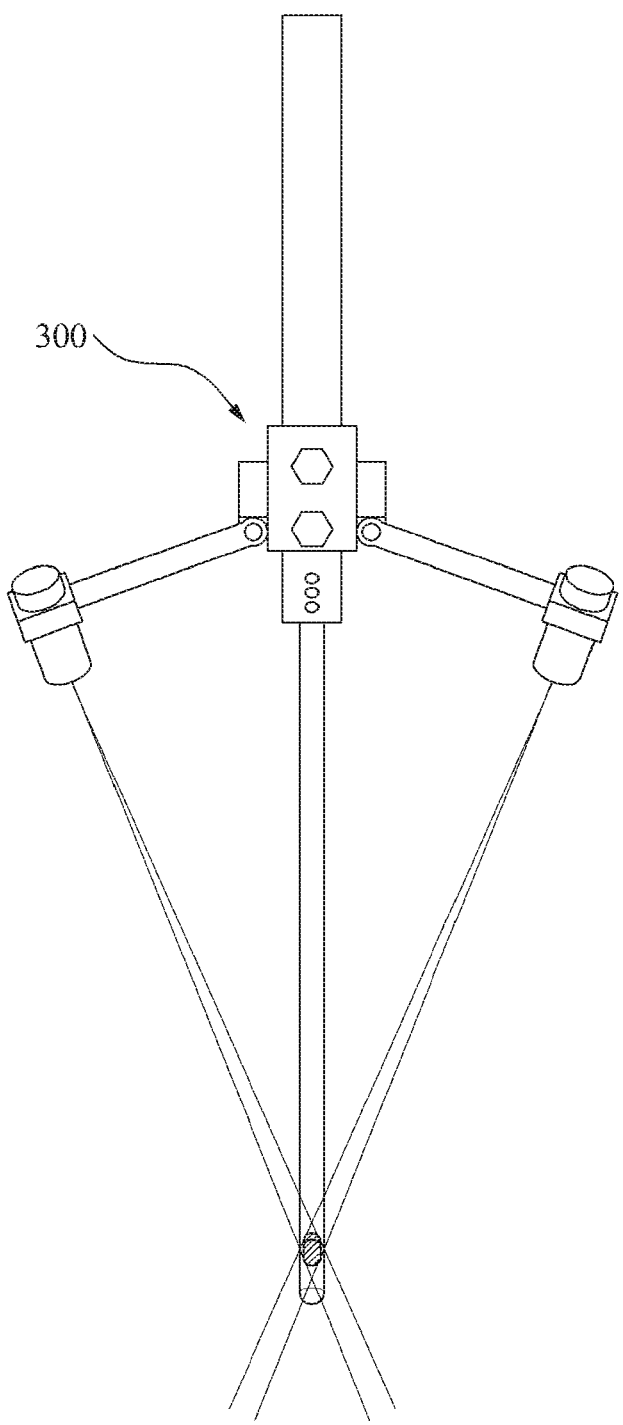
FIG. 4 is a left-side view illustrating the bone fixation apparatus of FIG. 1 including the position indicating apparatus to operate to indicate a position for an operation.

Referring to FIG. 4, a light radiated from the first light radiator 330*a* of the marker module 300 and a light radiated from the second light radiator 330*b* of the marker module 300 may form an intersection line. For example, the intersection line may be corrected to pass the second screw bore 220 formed at a lower end of the nail 200. In this example, the intersection line may indicate a position of the second screw bore 220 at an angle at which the second screw bore 220 of the nail 200 is not be seen. Through this, the marker module may accurately indicate a position without need to apply a physical force directly to a target body.

Referring to FIGS. 2 and 3, the first light radiator 330*a* may be adjustable in angle based on a longitudinal axis of the first arm 320*a*, and the second light radiator 330*b* may be adjustable in angle based on a longitudinal axis of the second arm 320*b*. The first arm 320*a* and the second arm 320*b* may respectively accept the first light radiator 330*a* and the second light radiator 330*b* and include tilting members 370*a* and 370*b* configured to rotate in a longitudinal direction of the first arm 320*a* and a longitudinal direction of the second arm 320*b*. The tilting members 370*a* and 370*b* may include receivers to accept the first light radiator 330*a* and the second light radiator 330*b*, respectively. The receivers may be provided in shapes corresponding to the shapes of the first light radiator 330*a* and the second light radiator 330*b* in order to accept the first light radiator 330*a* and the second light radiator 330*b*. Also, the tilting members 370*a* and 370*b* may be arranged using connecting members (not shown) rotatably connected to one end of the first arm 320*a* and one end of the second arm 320*b*.

As described above, the first light radiator 330*a* and the second light radiator 330*b* may be adjustable in angle based on the symmetric axis XX' of the main body 310 and adjustable in angle based on the longitudinal axes of the first arm 320*a* and the second arm 320*b*. Thus, a correction operation may be performed to indicate a desired position. The nail 200 may be formed in a different shape for each manufacturer. Also, even when the nail 200 is formed by the same manufacturer, a high accuracy is required and it may not be ensured that the second screw bore 220 is present at the same position. Thus, the first light radiator 330a and the second light radiator 330b may be configured to be adjustable in angle and a correction may be performed to accurately indicate a position before starting an operation. Through this, an error in the operation may be reduced and the precision of the operation may increase.

The first light radiator 330a and the second light radiator 330b may each include a laser radiator. When the first light radiator 330a and the second light radiator 330b radiate lasers, the lasers may form an intersection line. In this example, the intersection line may indicate a position of the second screw bore 220 provided at a lower end of the nail 200. By using the lasers, the correction may be performed to indicate the position before insertion of the nail 200 irrespective of influences of ambient lights.

Figure 5:
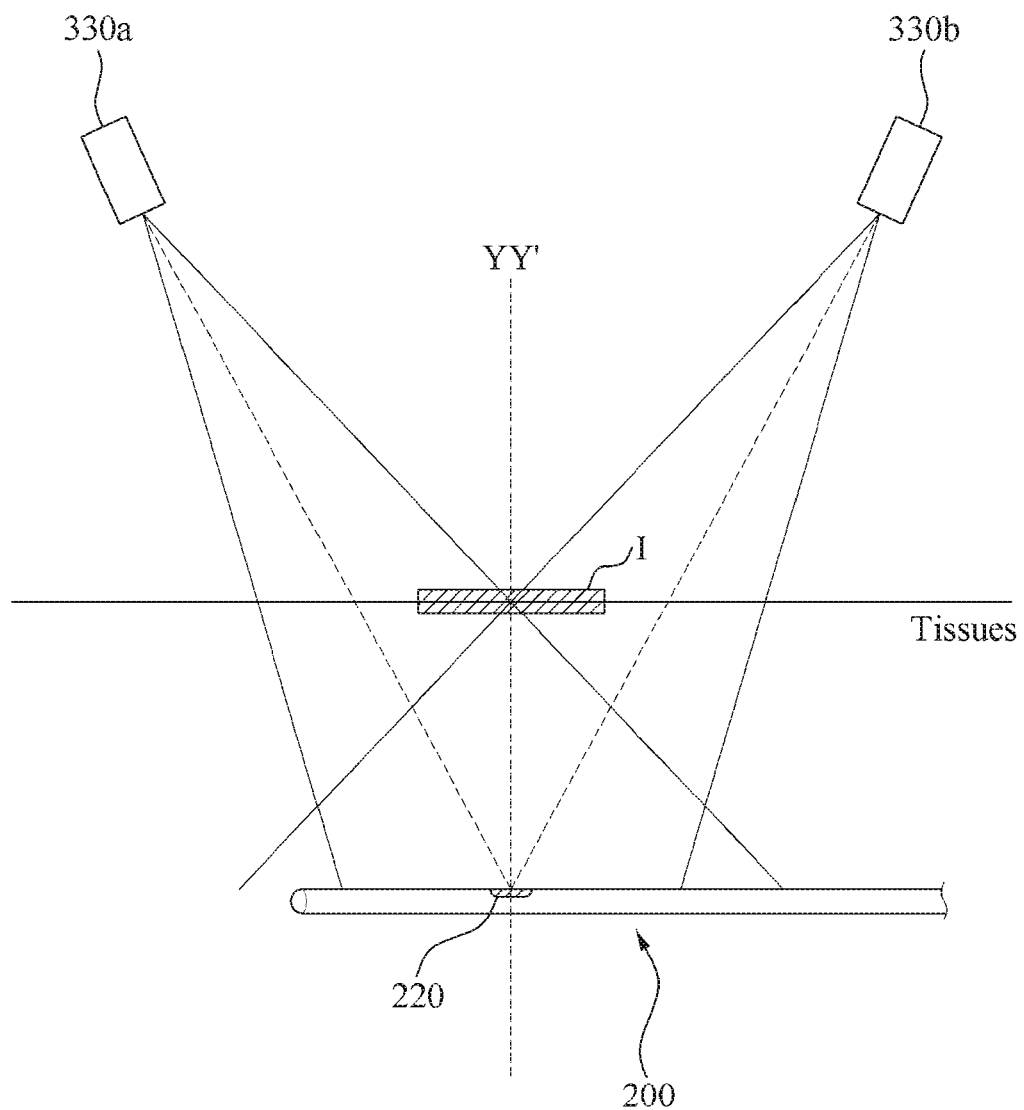
FIG. 5 is a view illustrating a bone fixation apparatus indicating a position using an intersection line formed by lights radiated from a light radiator to meet each other and an operation principle of the bone fixation apparatus according to an example embodiment.

The first light radiator 330a and the second light radiator 330b may radiate a linear beam. In this disclosure, the linear beam is a beam promoting in a straight line and, more specifically, is a beam forming a plane on which linear beams meet to form an intersection line. Referring to FIG. 5, the first light radiator 330a and the second light radiator 330b radiate linear beams. Also, the linear beams may form an intersection line YY' to penetrate a center of an incision part I. As shown in the drawing, body tissues may be incised such that the fixing screw is inserted to the second screw bore 220 through a drilling.

Additionally, the marker module 300 may further include a radiation adjuster (not shown) configured to acquire shape data of the nail 200 through a three-dimensional (3D) scanning and correct motions of the first arm 320a, the second arm 320b, and the tilting members 370a and 370b based on the shape data of the nail 200. Specifically, the shape data indicating a bending angle or a tilting angle, which may cause an error in position indication of the bone fixation apparatus 1, of the nail 200 may be acquired through the 3D scanning. Based on the shape data acquired through the 3D scanning, the radiation adjuster may control the motions, for example, rotation angles of the first arm 320a, the second arm 320b, and the tilting members 370a and 370b so as to correct radiation angles and positions of the first light radiator 330a and the second light radiator 330b to correspond to the nail 200. For this, a motor connected to each of the first arm 320a, the second arm 320b, and the tilting members 370a and 370b may be additionally provided. The radiation adjuster may control the motor to correct the radiation angles and positions of the first light radiator 330a and the second light radiator 330b based on the nail 200.

Hereinafter, a bone fixation system including the bone fixation apparatus 1 will be described with reference to FIGS. 6 through 9.

Figure 6:
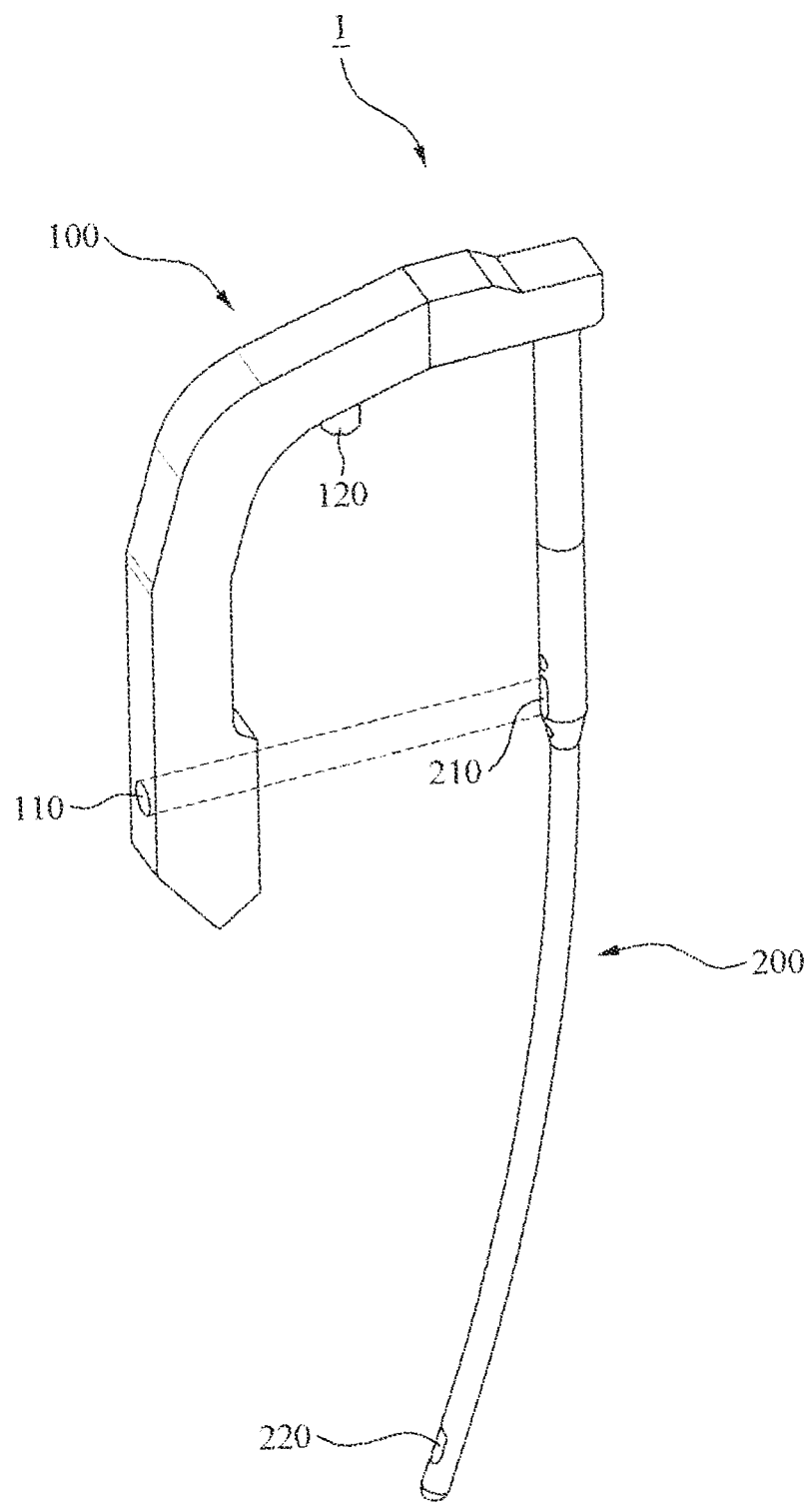
FIG. 6 is a perspective view illustrating a bone fixation apparatus including a targeting guide and a nail connected to the targeting guide according to an example embodiment.

Referring to FIG. 6, the targeting guide 100 or the nail 200 may further include an intramedullary nail posture detector 120 configured to measure nail posture information. A screw bore may include the first screw bore 210 and the second screw bore 220. Hereinafter, it is described that the screw bore indicates the second screw bore 220 for ease of description.

When the nail 200 is inserted into a body and a position of the intramedullary nail posture detector 120 is to be adjusted, the intramedullary nail posture detector 120 may be attached to one side of the targeting guide 100. The intramedullary nail posture detector 120 may include an inertial sensor to measure the nail posture information including an acceleration of gravity, an angular velocity, or a magnetic field. The initial sensor may be, for example, a 9-axis inertial sensor. The intramedullary nail posture detector 120 may measure an acceleration of gravity, an angular velocity, or a magnetic field with respect to three axes of the nail 200.

The bone fixation system may include a processor unit (not shown) and a communicator (not shown). The processor unit (not shown) may be configured to convert the mail posture information measured by the intramedullary nail posture detector 120 to insertion incidence angle information associated with the screw bore 220 such that a drill insertion path is aligned with the screw bore 220. The communicator (not shown) may be configured to transmit the insertion incidence angle information obtained by the processor unit.

For example, the processor unit (not shown) and the communicator (not shown) may be included in a separate apparatus or system. Also, the processor unit (not shown) and the communicator (not shown) may be included in the intramedullary nail posture detector 120. In this example, the nail posture information measured by the inertia sensor may be transmitted to the processor unit. The transmitted nail posture information may be converted into insertion incidence angle information of a drill 400 such that the screw bore 220 is aligned with an insertion path. The insertion incidence angle information may be transmitted to an indicator 600 or a display (not shown) such that an operator intuitively recognizes the insertion path.

The bone fixation system may further include the display (not shown). The display may receive the insertion incidence angle information from the communicator (not shown) and display the received insertion incidence angle information based on a roll value, a pitch value, or a yaw value. Also, the display may display the insertion incidence angle information when the insertion path of the drill is accurately aligned with the screw bore. For example, when the pitch or yaw value of the drill posture information or the insertion incidence angle information corrected based on the roll or yaw value corresponding to the nail posture information is close to a target value, a circle may appear at one end of a drill displayed on the display. Also, when the pitch or yaw value is out of the target value, the circle may disappear. Accordingly, by acquiring basic information associated with the roll, pitch, or yaw, or a presence or an absence of the circle, an error of the insertion path of the drill 400 with respect to the screw bore 220 may be reduced when the operator inserts the fixing screw into the screw bore 220 using the drill and thus, side effects of an operation may also be reduced.

Figure 7:
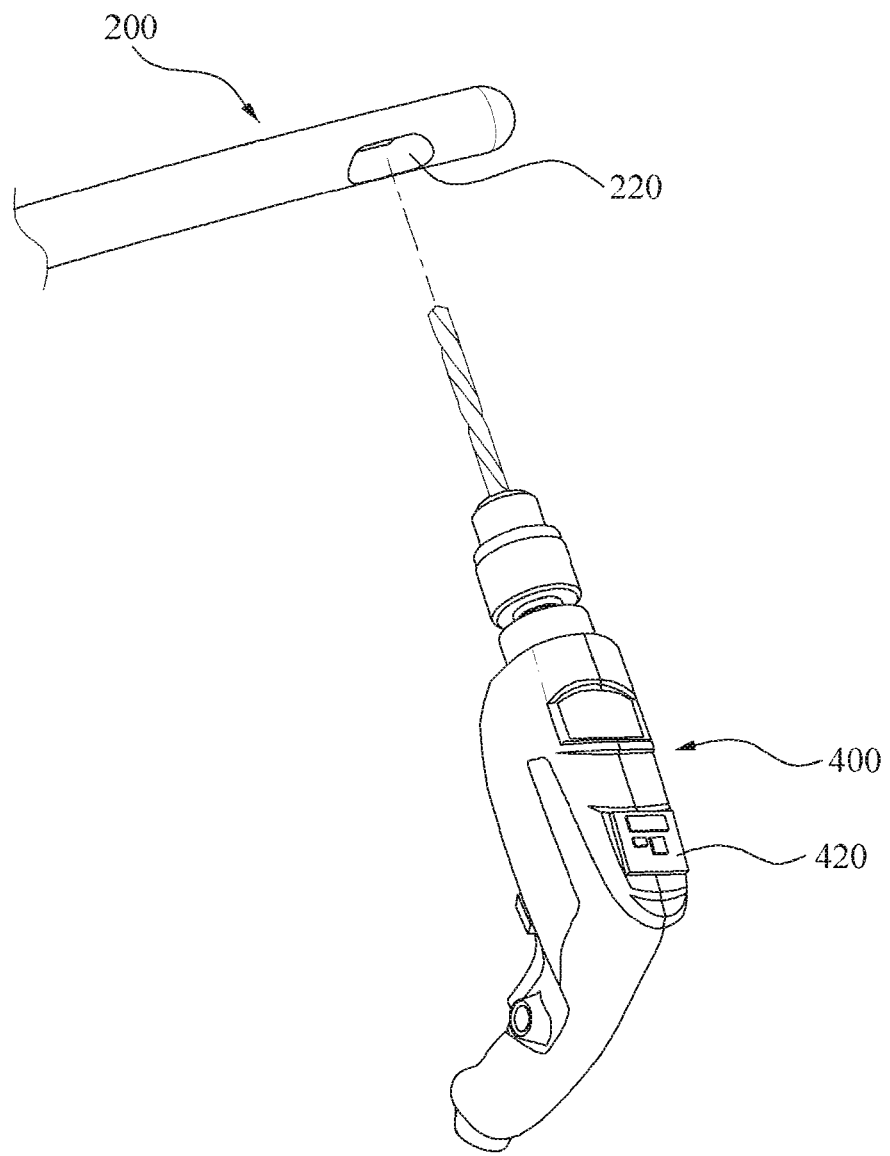
FIG. 7 is a view illustrating an example of inserting a fixing screw into a screw bore of a nail of a bone fixation apparatus according to an example embodiment.
Figure 8:
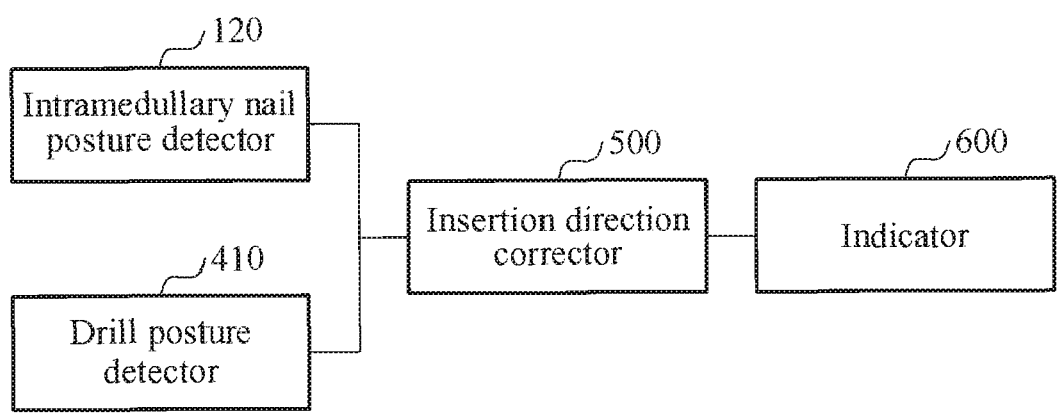
FIG. 8 is a block diagram illustrating a bone fixation system including intramedullary nail posture detector, a drill posture detector, an insertion direction corrector, and a display, which are connected to one another according to an example embodiment.
Figure 9:
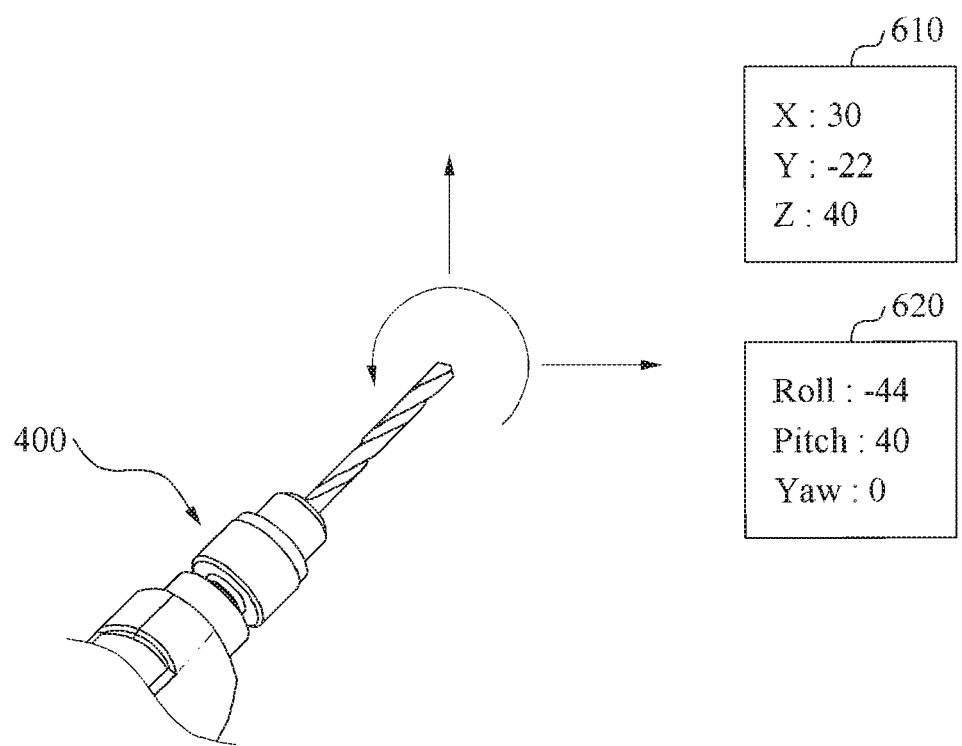
FIG. 9 is a view illustrating an example of drill posture information or nail posture information displayed on a display based on an insertion direction of a drill in a bone fixation system according to an example embodiment.

Hereinafter, a bone fixation system to improve an insertion accuracy will be described with reference to FIGS. 7 through 9.

The bone fixation system may include the targeting guide 100, the nail 200 having one end connected to the targeting guide 100 and the screw bore 220 at the other end, and the drill 400 inserting a fixing screw into the screw bore 220.

As described above, the targeting guide 100 or the nail 200 may include the intramedullary nail posture detector 120 configured to measure nail posture information. The intramedullary nail posture detector 120 may be attached to one side of the targeting guide 100. The intramedullary nail posture detector 120 may include an inertial sensor to measure the nail posture information including an acceleration of gravity, an angular velocity, or a magnetic field. The initial sensor may be, for example, a 9-axis inertial sensor.

The intramedullary nail posture detector 120 may measure an acceleration of gravity, an angular velocity, or a magnetic field with respect to three axes of the nail 200.

The drill 400 may include a drill posture detector 410 to measure drill posture information. The drill 400 may correct an insertion direction of the drill 400 with respect to the screw bore 220 based on the nail posture information and the drill posture information.

Similarly to the intramedullary nail posture detector 120, the drill posture detector 410 may include an inertial sensor to measure the drill posture information including an acceleration of gravity, an angular velocity, or a magnetic field. The initial sensor may be, for example, a 9-axis inertial sensor. The intramedullary nail posture detector 120 may measure an acceleration of gravity, an angular velocity, or a magnetic field with respect to three axes of the drill 200.

Additionally, the drill posture detector 410 may measure the insertion direction of the drill 400 in real time. As described below, the real-time measured insertion direction of the drill 400 may be used as basic information to be converted into the insertion incidence angle information of the drill 400.

The bone fixation system may include an insertion direction corrector 500 to correct the insertion direction of the drill 400 with respect to the screw bore 220 based on the nail posture information measured by the intramedullary nail posture detector 120 and the drill posture information measured by the drill posture detector 410.

The insertion direction corrector 500 may be disposed on one side of the drill 400 together with the indicator 600 in consideration of the indicator 600 being disposed on the one side of the drill 400. Also, the insertion direction corrector 500 and the indicator 600 may be provided as an integrated module.

The insertion direction corrector 500 may convert the nail posture information into insertion direction information. Through this, the insertion path of the drill 400 may be aligned with the screw bore 220 so as to increase the insertion accuracy.

The insertion direction corrector 500 may correct the insertion direction such that the yaw value of the nail posture information is perpendicular to the yaw value of the drill posture information. The roll and yaw values of the nail posture information may represent a direction in which a plane including the screw bore 220 is tilted and a degree to which the plane is tilted. The roll and yaw values of the drill posture information may represent a degree to which a plane including the insertion path of the drill 400 is tilted. Thus, when the yaw value of the nail posture information is perpendicular to the yaw value of the drill posture information, the plane including the screw bore 220 may be orthogonal to the insertion path of the drill 400. Through this, the insertion path of the drill 400 may be aligned with the screw bore 220 so as to increase the insertion accuracy.

As described above, when the insertion direction is measured by the drill posture detector 410 in real time, the insertion direction corrector 500 may perform conversion to obtain the insertion incidence angle information of the drill 400 based on the real-time measured insertion direction. For example, initially, the operator may position a drill based on the roll value of the nail posture information and the pitch value of the drill posture information such that an insertion point of the drill is aligned with the screw bore 220 of the nail. Thereafter, the operator may insert the fixing screw into the screw bore 220 such that the yaw value of the drill posture information is perpendicular to the yaw value of the nail posture information. In this example, when the operator is not a robot but a person, an error may occur in real time. Thus, the insertion direction may need to be measured in real time. When the insertion direction is measured by the drill posture detector 410 in real time, the operator may intuitively recognize the insertion incidence angle information and thus, the insertion accuracy may increase.

The bone fixation system may further include an indicator to provide the measured nail posture information, the measured drill posture information, the converted insertion direction information, or the converted insertion incidence angle information. The indicator 600 may be a display (not shown). The indicator 600 may be disposed on one side of the drill 400 such that the operator immediately recognizes the aforementioned information while inserting the fixing screw into the screw bore 220. Referring to FIG. 9, information on rotation directions and directions of two axes may be displayed on a plane that meets the insertion path of the drill 400. In one example, when the insertion incidence angle information of the drill, or a pitch value or a yaw value of the drill 400 reaches a predetermined target value corresponding to an error allowable range, an insertion inducing circle or point that is a form to be intuitively recognized by the operator may appear on the indicator 600. Also, a direction inducing a posture for insertion of the drill may appear on the indicator 600 such that the insertion incidence angle information of the drill reaches the target value corresponding to an error allowable range. The target value and the error allowable range may be previously set by a user as necessary. In another example, either or both position information 610 such as x, y, and z axes and rotation information 620 such as roll, pitch, and yaw axes may be displayed. The operator may control the insertion path of the drill 400 to be aligned with the screw bore 220 by referencing the position information, the rotation information 620, or an insertion inducing indication.

The drill 400 may further include a control unit 420 including the drill posture detector 410, the insertion direction corrector 500, or the indicator 600. The drill posture detector 410, the insertion direction corrector 500, or the indicator 600 may be provided separate from the drill 400, and also be included in the drill 400.

A surgical operation method using the bone fixation system for indicating a position for an operation will be described. Hereinafter, repeated description will be omitted.

The surgical operation method using the bone fixation system may include an operation of connecting the marker module 300 and an intramedullary nail including the targeting guide 100 and the nail 200 connected to one side of the targeting guide 100 and having the screw bore 220 at a lower end, an operation of correcting an intersection line that is formed by the lights radiated from the first light radiator 330a and the second light radiator 330b to be aligned with the screw bore 220 using the marker module 300 including a plurality of light radiators including the first light radiator 330a and the second light radiator 330b, an operation of incising a skin and inserting the nail 200 into an incision part, and an operation of inserting the fixing screw into a position indicated by the intersection line formed by the radiated lights.

The surgical operation method using the bone fixation system may further include an operation of correcting a direction in which the fixing screw is inserted into the screw bore based on the measured nail posture information and the measured drill posture information.

The surgical operation method using the bone fixation system may further include an operation of compensating for the direction in which the fixing screw is inserted into the screw bore such that the yaw value of the measured nail posture information is perpendicular to the yaw value of the measured drill posture information.

The surgical operation method using the bone fixation system may further include an operation of inserting the fixing screw by positioning a drill such that a drill insertion path is aligned with the screw bore in response to a compensation for the roll value and the yaw value of the measured nail posture information based on the pitch value and the yaw value of the measured drill posture information.

The surgical operation method using the bone fixation system may further include an operation of acquiring nail shape data through a 3D scanning and an operation of correcting insertion angle and position of the light radiator based on the nail shape data before the operation of connecting the marker module and the intramedullary nail.

Figure 10:
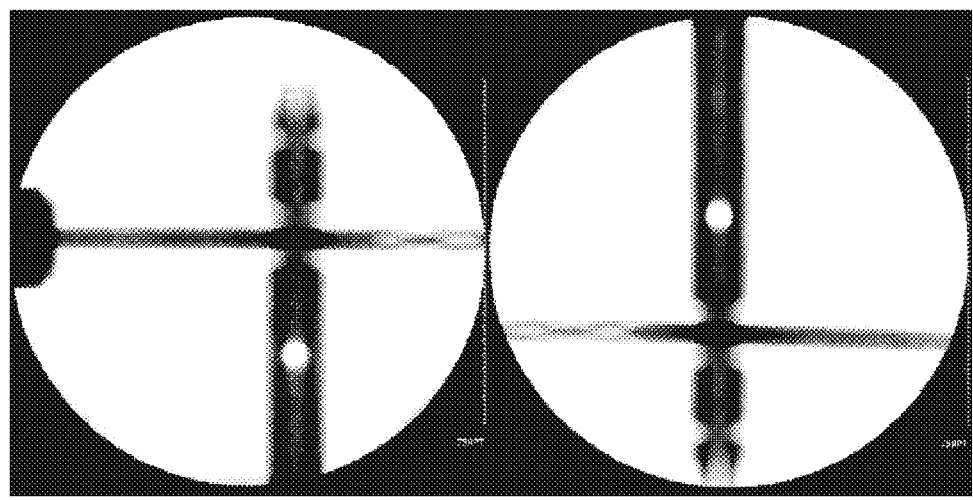
FIG. 10 is an X-ray view illustrating an experimental example in which an insertion accuracy of a drill is measured using a bone fixation apparatus in a surgical operation method using a bone fixation system according to an example embodiment.

Referring to FIG. 10, in an experimental example using femur sawbones, an accuracy on an operation of inserting a fixing screw into a screw bore was measured using a bone fixation apparatus for indicating a position for an operation.

Tables 1 through 3 show results of experiments in which the operation of inserting a fixing screw into a screw bore was performed with respect to a novice group and an expert group.

TABLE 1

|  | Mean | | Standard deviation | | Correlation between novice and expert |
|---|---|---|---|---|---|
|  | Novice | Expert | Novice | Expert | |
| Absolute value of angle (degree) | 2.25 | 2.92 | 1.10 | 1.66 | r = −.131, p = .489 |
| Absolute value of a (mm) | 2.16 | 1.92 | 1.26 | 1.15 | r = −.193, p = .308 |
| Absolute value of a (mm) | 2.49 | 2.29 | 1.37 | 1.22 | r = −.172, p = .363 |
| Absolute value of b − a (mm) | .43 | .56 | .21 | .32 | r = −.120, p = .526 |

Table 1 shows absolute values of angles compared between a novice group and an expert group when inserting a fixing screw into a screw bore. Here, the absolute value of angle represents a degree to which a drill insertion path is aligned with a screw bore.

It is found from the absolute value of angle that a tendency of a statistically meaningful difference between the two groups was observed, for example, [t(29)=−1.733, p=0.094] or no difference between the two groups was observed, for example, [t(29)=−1.733, p>0.05].

It may be found from the absolute value of a that no difference between the two groups was observed, for example, [t(29)=0.690, p=0.495 or p>0.05].

It may be found from the absolute value of b that no difference between the two groups was observed, for example, [t(29)=0.553, p=0.585 or p>0.05].

It may be found from the absolute value of b−a that a tendency of a statistically meaningful difference between the two groups was observed, for example, [t(29)=−1.815, p=0.080] or no difference between the two groups was observed, for example, [t(29)=−1.815, p>0.05].

The above result corresponds to "p>0.05" and thus, it can be known that no difference between the two groups was observed. That is, it is indicated that the novice group may perform a bone fixation operation using the bone fixation system similarly to the expert group.

TABLE 2

|  | Mean | | Standard deviation | | Correlation between the novices |
|---|---|---|---|---|---|
|  | Novice 1 | Novice 2 | Novice 1 | Novice 2 | |
| Absolute value of angle (degree) | 2.47 | 2.02 | 1.47 | 1.52 | r = .076, p = .691 |
| Absolute value of a (mm) | 1.84 | 2.47 | 1.57 | 1.69 | r = .196, p = .298 |
| Absolute value of a (mm) | 2.22 | 2.75 | 1.72 | 1.80 | r = .200, p = .290 |
| Absolute value of b − a (mm) | .48 | .38 | .28 | .29 | r = .061, p = .748 |

Table 2 shows absolute values of angles compared between novices. Here, the absolute value of angle represents a degree to which a drill insertion path is aligned with a screw bore.

It may be found from the absolute value of angle that no difference between the two novices was observed, for example, [t(29)=1.202, p=0.239 or p>0.05].

It may be found from the absolute value of a that no difference between the two novices was observed, for example, [t(29)=−1.663, p=0.107 or p>0.05].

It may be found from the absolute value of b that no difference between the two novices was observed, for example, [t(29)=−1.302, p=0.203 or p>0.05].

It may be found from the absolute value of b−a that no difference between the two novices was observed, for example, [t(29)=1.267, p=0.215 or p>0.05].

The above result corresponds to "p>0.05" and thus, it can be known that a technical ability may not be required for performing the bone fixation operation using the bone fixation system since no difference was observed in the novice group. That is, it is indicated that a less skilled novice may sufficiently perform the bone fixation operation using the bone fixation system as well as a skilled novice.

TABLE 3

|  | Mean | | Standard deviation | | Correlation between the experts |
|---|---|---|---|---|---|
|  | Expert 3 | Expert 4 | Expert 3 | Expert 4 | |
| Absolute value of angle (degree) | 3.35 | 2.48 | 2.19 | 2.11 | r = .190, p = .314 |
| Absolute value of a (mm) | 1.99 | 1.86 | 1.65 | 1.61 | r = −.001, p = .996 |
| Absolute value of b (mm) | 2.42 | 2.16 | 1.84 | 1.65 | r = −.117, p = .539 |
| Absolute value of b − a (mm) | .64 | .48 | .42 | .40 | r = .186, p = .324 |

Table 3 shows absolute values of angles compared between experts. Here, the absolute value of angle represents a degree to which a drill insertion path is aligned with a screw bore.

It may be found from the absolute value of angle that a tendency of a statistically meaningful difference between the two experts was observed, for example, [t(29)=1.750, p=0.091] or no difference between the two experts was observed, for example, [t(29)=1.750, p>0.05].

It may be found from the absolute value of a that no difference between the two experts was observed, for example, [t(29)=0.320, p=0.751 or p>0.05].

It may be found from the absolute value of b that no difference between the two experts was observed, for example, [t(29)=0.526, p=0.603 or p>0.05].

It may be found from the absolute value of b-a that a tendency of a statistically meaningful difference between the two experts was observed, for example, [t(29)=1.709, p=0.098] or no difference between the two experts was observed, for example, [t(29)=1.709, p>0.05].

The above result corresponds to "p>0.05" and thus, it can be known that a special technical ability may not be required for performing the bone fixation operation using the bone fixation system since no difference was observed in the expert group.

In summary, the experiment of measuring the accuracy of the operation was performed 45 times and there was no failure of the fixation screw insertion. A distance error measured from a center of the screw bore was within ±1.3 mm and a directional error was within ±3°. Through this, an operation time used for inserting the fixing screw into the screw bore may be significantly reduced and a radiation exposure time for both patient and surgeon may also be significantly reduced.

Hereinafter, an operation of a bone fixation system including a bone fixation apparatus will be described.

An operator may acquire shape data of the nail 200 through a 3D scanning.

Based on the shape data of the nail 200, an insertion point may be indicated on a predetermined position from an intersection line formed by lights radiated from the first light radiator 330a and the second light radiator 330b of the marker module 300

The first light radiator 330a and the second light radiator 330b may use the first arm adjusting member 340a and the second arm adjusting member 340b to adjust angles of the first arm 320a and the second arm 320b and adjust angles of the tilting members 370a and 370b respectively connected to one end of the first arm 320a and one end of the second arm 320b. Also, the first light radiator 330a and the second light radiator 330b may radiate the lights to the second screw bore 220 of the nail 200 based on shape data of the nail 200 acquired through a 3D scanning. Through this, the insertion point may be indicated at the predetermined position to pass through the second screw bore 220.

The operator may adjust the targeting guide 100 to insert the nail 200 into a desired body part.

The operator may insert a fixing screw penetrating the through bore 110 of the targeting guide 100 and the first screw bore 210 aligned with the through bore 110.

The operator may insert the fixing screw into the insertion point indicated on a skin of body tissues using the drill 400 to reach the second screw bore 220 obscured by the body tissues.

Thereafter, the nail posture information and the drill posture information may be measured by the intramedullary nail posture detector 120 and the drill posture detector 410. Based on the measured nail posture information and the measured drill posture information, an insertion direction of the drill 400 may be corrected such that an insertion path of the drill 400 is aligned with the second screw bore 220. In this example, the operator may verify whether the insertion path of the drill 400 is aligned with the second screw bore 220 based on the drill posture information using the indicator 600 in real time, which may allow an accurate insertion of the fixing screw.

A position indicating apparatus may accurately indicate a desired position using a light in various fields such as a construction field, a medical field, and a precise machine field and also indicate the position without applying a physical force directly to a target.

A bone fixation apparatus for indicating a position for an operation may accurately indicate a position of a hole to be drilled on a bone without radiography and indicate the position without restrictions on a space and costs.

A bone fixation apparatus for increasing an insertion accuracy and a bone fixation system including the bone fixation apparatus may significantly reduce a direction in which the drill is inserted into a body by measuring a posture of an intramedullary nail and a posture of a drill, and provide information on the drill insertion direction to an operator in an intuitively recognizable form.

A number of example embodiments have been described above. Nevertheless, it should be understood that various modifications may be made to these example embodiments. For example, suitable results may be achieved if the described to techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A position indicating apparatus comprising:
   a main body;
   a first arm rotatably connected to one side of the main body based on a symmetric axis of the main body;
   a second arm rotatably connected to another side of the main body based on the symmetric axis;
   a first light radiator connected to one end of the first arm to radiate a first light;
   a second light radiator connected to one end of the second arm to radiate a second light;
   a first arm adjusting member interposed between the main body and the first arm and configured to adjust a rotation angle of the first arm with respect to the main body;
   a second arm adjusting member interposed between the main body and the second arm configured to adjust a rotation angle of the second arm with respect to the main body;
   a first tilting member configured to receive the first light radiator and rotate about a longitudinal axis of the first arm, wherein the first tilting member is rotatably connected to the one end of the first arm; and
   a second tilting member configured to receive the second light radiator and rotate about a longitudinal axis of the second arm, wherein the second tilting member is rotatably connected to the one end of the second arm,
   wherein the first light radiated from the first light radiator and the second light radiated from the second light radiator meet and form an intersection of line,
   wherein the first arm and the second arm are adjustable in angle based on the symmetric axis of the main body, and
   wherein the first light radiator is adjustable in angle based on the longitudinal axis of the first arm by rotating the first tilting member about the longitudinal axis of the first arm, and the second light radiator is adjustable in angle based on the longitudinal axis of the second arm by rotating the second tilting member about the longitudinal axis of the second arm.

2. The position indicating apparatus of claim 1, wherein the first light radiator and the second light radiator are configured to rotate in a longitudinal direction and a lateral direction based on a first center of the first light radiator and a second center of the second light radiator.

3. The position indicating apparatus of claim 1, wherein the main body includes:
   a connecting hole formed internally; and
   locking guide holes formed on one side surface of the main body and another side surface opposite to the one side surface.

4. The position indicating apparatus of claim 1, wherein the first tilting member includes a first receiver configured to accept the first light radiator and having a shape corresponding to the shape of the first light radiator, and the second tilting member includes a second receiver configured to accept the second light radiator and having a shape corresponding to the shape of the second light radiator.

5. The position indicating apparatus of claim 1, wherein the first arm adjusting member and the second arm adjusting member are hinge-type adjusting members.

6. The position indicating apparatus of claim 1, wherein each of the first arm adjusting member and the second arm adjusting member includes an elastic body.

7. The position indicating apparatus of claim 1, further comprising an angle adjustable motor configured to control the first arm adjusting member and the second arm adjusting member.

\* \* \* \* \*